United States Patent [19]

Machida et al.

[11] Patent Number: 4,613,218
[45] Date of Patent: Sep. 23, 1986

[54] ILLUMINATING LIGHT BEAM AXIS ADJUSTING MECHANISM IN OPHTHALMOSCOPE WITH PHOTOGRAPHING DEVICE

[75] Inventors: Takeshi Machida; Takashi Komori, both of Tokyo, Japan

[73] Assignee: Asahi Kogaku Kogyo Kabushiki Kaisha, Tokyo, Japan

[21] Appl. No.: 536,796

[22] Filed: Sep. 28, 1983

[30] Foreign Application Priority Data

Sep. 28, 1982 [JP] Japan .......................... 57-146725[U]

[51] Int. Cl.⁴ ........................... A61B 3/14; A61B 3/10
[52] U.S. Cl. ..................................... 351/206; 351/205
[58] Field of Search ............... 351/205, 206, 207, 208, 351/221

[56] References Cited

U.S. PATENT DOCUMENTS 3,915,564 10/1975 Urban .................................. 351/206
4,149,787 4/1979 Kobayashi et al. ............. 351/206 X
4,235,529 11/1980 Kawase ................................ 351/206

*Primary Examiner*—Rodney B. Bovernick
*Attorney, Agent, or Firm*—Sughrue, Mion, Zinn, Macpeak and Seas

[57] ABSTRACT

An apparatus for adjusting a direction of an illuminating light beam in an ophthalmoscope which contains a photographing device includes a click stop mechanism which click stops rotation of a mirror used to reflect the illuminating light beam so that the light beam is accurately reflected onto a photographic film in the photographing device. A knob is integrally connected to a rotary shaft which is rotatably coupled to a mirror frame so that rotation of the knob rotates the mirror frame, and an interlocking member is fixedly disposed on the rotary shaft and contains a click ball mechanism which selectively engages a hole in an outer frame so that rotation of the rotary shaft is click stopped at a predetermined position.

4 Claims, 2 Drawing Figures

ILLUMINATING LIGHT BEAM AXIS ADJUSTING MECHANISM IN OPHTHALMOSCOPE WITH PHOTOGRAPHING DEVICE

BACKGROUND OF THE INVENTION

The present invention relates to a mechanism for adjusting the direction of an illuminating light beam in an ophthalmoscope which contains a photographing device.

In an ophthalmoscope, the direction of an illuminating light beam is adjusted by rotating a mirror while an object is being observed. The additions of a photographing device to the ophthalmoscope (which has not yet been disclosed in the art) presents a problem in that the center of the illumination range or the center of the object is shifted from the center of the picture frame of the film. Furthermore, if the axis of the illuminating light beam is fixed in alignment with the optical axis of the photographing device, then the light beam axis cannot be finely adjusted when the object is only being observed with the ophthalmoscope and not being photographed.

SUMMARY OF THE INVENTION

The present invention provides a simple mechanism for engaging and disengaging click stop means in a rotary member which is used for rotating the illuminating mirror in an ophthalmoscope which contains a photographing device. Rotation of the illuminating mirror is click stopped at a predetermined position which is suitable for photographing, and the mirror can be further rotated and finely adjusted during visual observation by disengaging the click stop means.

Specifically, an apparatus for adjusting the direction of an illuminating light beam in an ophthalmoscope which contains a photographing device includes means for rotating a mirror for reflecting an illuminating beam which originates from a light source, and click stop means for click stopping rotation of the mirror at a predetermined position when a photographing operation is to be conducted. The rotating means and the click stop means include a rotary shaft which is integrally coupled to a knob, the rotary shaft being axially, slidably fitted into an outer frame and into a mirror frame, and an interlocking member is formed on the rotary shaft. The interlocking member contains a hole which receives a click ball which is biased radially outwardly of the hole by a spring, and the click ball selectively engages a further hole formed in the outer frame when the rotary shaft is in a predetermined axial position.

DESCRIPTION OF THE PREFERRED EMBODIMENTS

Figure 1:
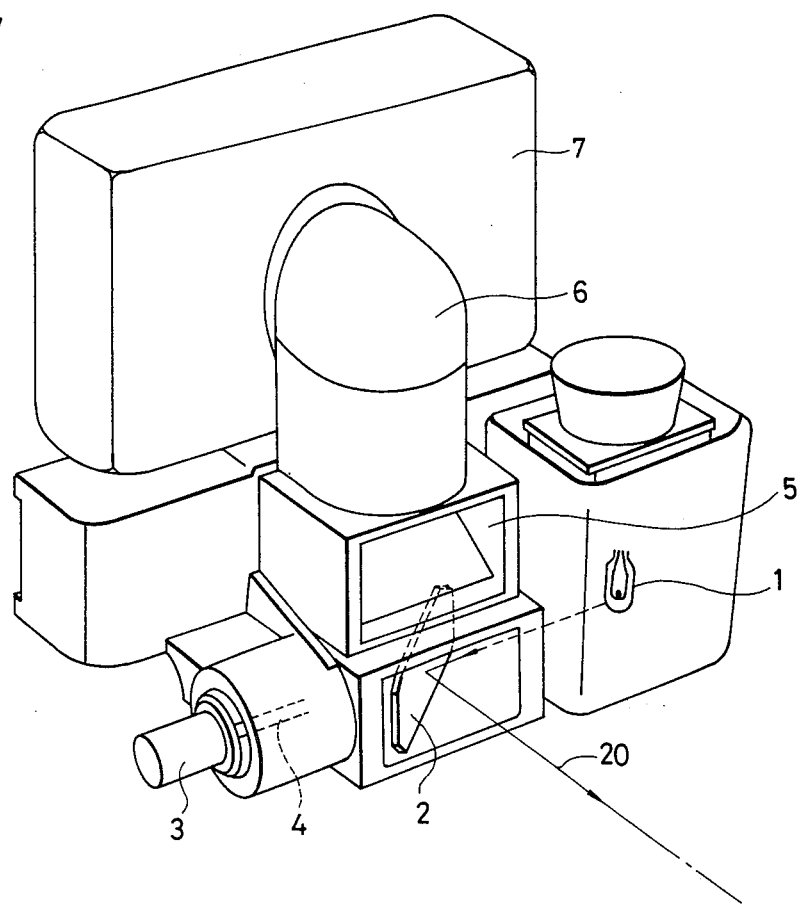
FIG. 1 is a perspective view showing an opthalmoscope which contains a photographing device.

FIG. 1 is a perspective view showing an ophthalmoscope which contains a photographing device. An illuminating light beam 20 which originates from an illuminating light source 1 is reflected by an illuminating mirror 2, and a knob 3 is turned to rotate a rotary shaft 4 and the illuminating mirror 2 to adjust the direction of the axis of the light beam so that the light beam is reflected toward an eye to be examined. The light beam, which has been reflected toward and from the eye, enters an observing (and photographing) window 5, and a part of the light beam reaches a camera 7 through photographing lens 6 during a photographing operation.

Figure 2:
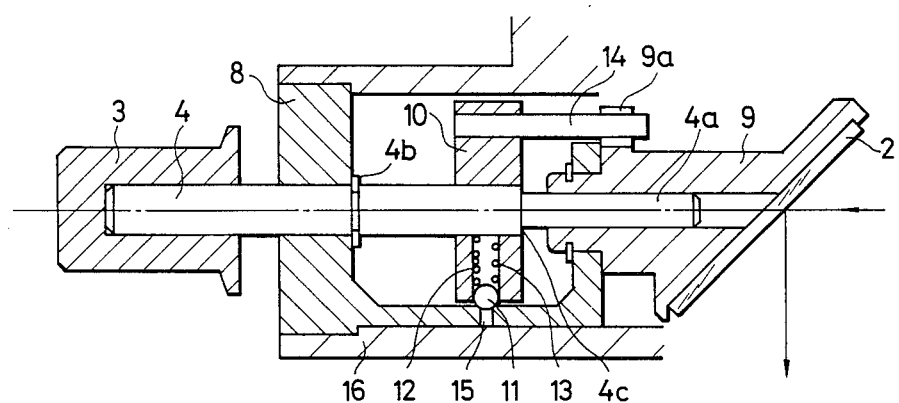
FIG. 2 is a sectional view showing an illuminating light beam axis adjusting mechanism according to one embodiment of the present invention.

FIG. 2 is a sectional view of the essential parts of the ophthalmoscope according to the present invention. The rotary shaft 4 is integral with the knob 3 and is rotatably and slidably supported by an outer frame 8, and a front end portion 4a of the shaft 4 is slidably supported by a mirror frame 9 which is used to mount the illuminating mirror 2. An interlocking member 10 is fixedly mounted on a middle portion of the rotary shaft 4, and the rotary shaft 4 contains a shoulder 4c for engaging a front end of the mirror frame 9 and for limiting axial movement of the rotary shaft in one direction. A stopper 4b, which is located on the rotary shaft, limits axial movement of the rotary shaft in the opposite direction, and the member 10 contains a hole 12 into which a click ball 11 is inserted. Furthermore, a spring 13 is inserted into the hole 12 to push the click ball 11 radially outward. A pin 14 is embedded in the interlocking member 10, and this pin is engaged with a groove 9a cut into the mirror frame 9 so that rotation of the rotary shaft 4 is transmitted to the mirror frame 9. In this connection, it should be noted that the pin 14 is slidable in the groove 9a. The mirror frame 9 is supported by the outer frame 8 so that neither frame interferes with the sliding of the rotary shaft 4, and the outer frame 8 contains a hole 15 into which the click ball 11 drops in a clicking motion when the illuminating mirror 2 is inclined at an angle that is best suited for photographing. In FIG. 2, reference numeral 16 designates a cover.

The operation of the ophthalmoscope which contains the photographing device will now be described. When photographing an object such as an eye, the knob 3 is pulled until the stopper 4b of the rotary shaft 4 abuts against the outer frame 8, and the knob 3 is then turned to activate the clicking mechanism. Thus, after the object has been aligned with the axis of the illuminating light beam, it is photographed. In order to observe the object, the knob is pushed so that the rotary shaft 4 slides in the axial direction in order to release the clicking mechanism. In this position, the object may be observed while the knob 3 is being turned to finely adjust the angle of the illuminating mirror 2. When the knob 3 is pushed in, the rotary shaft 4 slides until its shoulder 4c abuts against the mirror frame 9. As is evident, the rotary shaft slides along an axial direction from a position at which the stopper 4b abuts against the outer frame 8 to a position at which the shoulder 4c abuts against the mirror frame 9. If the shaft 4 slides within this range, the angle of the mirror frame 9 can be finely adjusted without being affected by the sliding of the shaft 4 when the knob is pushed or pulled.

As is apparent from the above description, according to the illuminating light beam axis adjustment of the present invention, the axis of the illuminating light beam is set in a desired position during the photographing operation by means of the clicking mechanism to allow the image of the object to come to the center of the picture frame of the film, and, in the observing operation, the clicking mechanism is released to permit fine adjustment of the axis of the illuminating light beam.

We claim:

1. In an ophthalmoscope having a light source, a photographing device, and a mirror for reflecting and illuminating light beam originating from the light source, said mirror being rotatable between at least a normal, visual viewing position and a distinct photographing position, an apparatus for adjusting a direction of travel of the illuminating light beam, comprising;
   a mirror frame for holding said mirror;
   an outer frame;
   means for rotating said mirror, said rotating means comprising a knob, a rotary shaft integrally coupled to said knob and axially slidably fitted in said outer frame and said mirror frame, and means for transmitting rotation of said rotary shaft to said mirror frame to rotate said mirror; and
   stop means associated with said mirror rotating means for stopping rotation of said mirror at a predetermined position suitable for conducting a photographic operation, said stop means comprising an interlocking member fixedly attached to said rotary shaft, said interlocking member having a hole therein, a click ball disposed in said hole, and means for biasing said click ball radially outwardly against an inner surface of said outer frame.

2. The apparatus as claimed in claim 1, wherein said biasing means comprises a spring, said inner surface of said outer frame having a hole therein for engaging said click ball when said rotary shaft and said interlocking member are at a predetermined axial and radial position.

3. The apparatus as claimed in claim 2, wherein said rotating means further comprises a pin engaged with a groove formed in said mirror frame, said pin being fixed to said interlocking member.

4. The apparatus as claimed in claim 3, wherein a front end portion of said rotary shaft is slidably supported by said mirror frame, said rotary shaft having a stopper attached thereto which selectively engages said outer frame and limits axial movement of said rotary shaft in one direction, said rotary shaft having a shoulder formed thereon which selectively engages said mirror frame and limits axial movement of said rotary shaft in a second opposite direction, one of said shoulder and said stopper being positioned on said rotary shaft such that said click ball can engage said hole in said outer frame when said rotary shaft has been moved along said axial direction a distance such that one of said stopper and said shoulder abuts one of said outer frame and said mirror frame, respectively.

* * * * *